(12) United States Patent
Peukert et al.

(10) Patent No.: US 8,192,496 B2
(45) Date of Patent: Jun. 5, 2012

(54) INTERVERTEBRAL IMPLANT AND HANDLING INSTRUMENT FOR THIS INTERVERTEBRAL IMPLANT

(75) Inventors: Andrea Peukert, Tuttlingen (DE); Stephan Lindner, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 239 days.

(21) Appl. No.: 12/655,189

(22) Filed: Dec. 22, 2009

(65) Prior Publication Data
US 2010/0179660 A1    Jul. 15, 2010

(30) Foreign Application Priority Data

Jan. 15, 2009 (DE) .......................... 10 2009 004 730

(51) Int. Cl.
*A61F 2/44* (2006.01)
(52) U.S. Cl. ............... 623/17.15; 623/17.11; 623/17.14; 623/17.16
(58) Field of Classification Search ..... 623/17.11–17.16
See application file for complete search history.

(56) References Cited

U.S. PATENT DOCUMENTS

| | | | | |
|---|---|---|---|---|
| 5,571,189 | A * | 11/1996 | Kuslich .................... | 623/17.12 |
| 6,063,121 | A * | 5/2000 | Xavier et al. .............. | 623/17.15 |
| 7,087,083 | B2 * | 8/2006 | Pasquet et al. ............. | 623/17.11 |
| 7,354,453 | B2 * | 4/2008 | McAfee ..................... | 623/17.16 |
| 7,704,280 | B2 * | 4/2010 | Lechmann et al. ........ | 623/17.15 |
| 2004/0093087 | A1 * | 5/2004 | Ferree et al. ............... | 623/17.13 |
| 2004/0117017 | A1 * | 6/2004 | Pasquet et al. ............. | 623/17.11 |
| 2005/0143821 | A1 | 6/2005 | Zdeblick et al. | |
| 2006/0229724 | A1 * | 10/2006 | Lechmann et al. ........ | 623/17.11 |
| 2006/0247778 | A1 * | 11/2006 | Ferree et al. ............... | 623/17.14 |
| 2007/0093897 | A1 * | 4/2007 | Gerbec et al. ............. | 623/17.11 |
| 2007/0209222 | A1 * | 9/2007 | Fischer et al. ............. | 33/512 |
| 2009/0182432 | A1 | 7/2009 | Zdeblick et al. | |
| 2010/0204798 | A1 * | 8/2010 | Gerbec et al. ............. | 623/17.16 |

FOREIGN PATENT DOCUMENTS

| | | |
|---|---|---|
| DE | 20 2004 014 120 | 11/2004 |
| DE | 600 18 924 | 4/2006 |
| EP | 1 648 351 | 4/2006 |
| WO | 2008/048851 | 4/2008 |

\* cited by examiner

*Primary Examiner* — Eduardo C Robert
*Assistant Examiner* — Ellen C Hammond
(74) *Attorney, Agent, or Firm* — Lipsitz & McAllister, LLC (57) ABSTRACT

In an intervertebral implant having an abutment element for abutment on at least one vertebral body, in order to be able to apply pulling forces to the abutment element without the risk of damage to the abutment element, it is proposed that the abutment element carry at a side edge a pull element which extends along the side wall of the abutment element and is held on the abutment element by pull members extending at the sides of the abutment element in the direction towards the opposite side edge, the pull element being made of a material whose tensile strength is greater than the tensile strength of the material of the abutment element, and that an interspace for receiving a handling instrument engaging the pull element from behind be arranged at least in a section along the pull element between the pull element and the abutment element. A handling instrument for handling such an intervertebral implant is also described.

13 Claims, 9 Drawing Sheets

INTERVERTEBRAL IMPLANT AND HANDLING INSTRUMENT FOR THIS INTERVERTEBRAL IMPLANT

The present disclosure relates to the subject matter disclosed in German application number 10 2009 004 730.1 of Jan. 15, 2009, which is incorporated herein by reference in its entirety and for all purposes.

BACKGROUND OF THE INVENTION

The invention relates to an intervertebral implant having an abutment element for abutment on at least one vertebral body.

Such intervertebral implants are inserted into intervertebral spaces after removal of an intervertebral disc. To do so, it is necessary to grasp such an abutment element with a handling instrument in order that it can be inserted in the correct position into the intervertebral space.

The insertion is relatively easy, but difficulties may occur during the extraction, particularly when an intervertebral implant has to be removed again after a considerable time in situ. Considerable pulling forces then have to be applied to the abutment element or the abutment elements, and problems occur, particularly in the case of small intervertebral implants in the area of the cervical vertebrae and also when materials that do not have a very high strength are used for the abutment element. When the abutment element is grasped directly with a tong-shaped or clamp-type handling instrument, there is the risk that the abutment element will break away, that pieces of material will be torn off or that the entire abutment element will break.

The object of the invention is to so construct a generic intervertebral implant that even when materials that do not have a high strength are used for the abutment element, or the abutment element is of small structural size, high pulling forces can still be applied to the abutment element, if necessary, in order to extract it from its position in an intervertebral space.

SUMMARY OF THE INVENTION

This object is accomplished, in accordance with the invention, in an intervertebral implant of the kind described at the outset in that the abutment element carries at a side edge a pull element which extends along the side wall of the abutment element and is held on the abutment element by pull members extending at the sides of the abutment element in the direction towards the opposite side edge, the pull element being made of a material whose tensile strength is greater than the tensile strength of the material of the abutment element, and in that an interspace for receiving a handling instrument engaging the pull element from behind is arranged at least in a section along the pull element between the pull element and the abutment element.

Accordingly, the abutment element is provided with an additional pull element which extends along a side edge and has a high strength. It is to be assumed that the tensile strength of the pull element is at least twice as large as the tensile strength of the material from which the abutment element is made. In particular, the abutment element may consist of metal, for example, of titanium, but it is also possible to use plastic materials which are compatible with the body and to produce a pull element from carbon fiber reinforced-polyetheretherketone.

The tensile strength should lie in the range of between 500 and 3000 N/mm$^2$, the tensile strength of titanium being about 1000 N/mm$^2$. In other possible metal alloys, for example, a cobalt-chromium-nickel alloy, tensile strengths of between 800 and 2500 N/mm$^2$ are attainable, depending on what pretreatment has been performed. In the case of plastic materials which are compatible with the body, the tensile strength is significantly lower, namely, as a rule, in the range of between 80 and 300 N/mm$^2$.

An interspace is provided at least in a section between the pull element and the abutment element, so that a handling instrument can access this interspace and engage the pull element from behind. The pull element itself is held on the abutment element by pull members engaging the pull element at the sides and extending along the side surfaces on the abutment element.

The pulling forces are, therefore, transmitted via the pull element and the pull members onto the abutment element and not via any very small parts of the abutment element itself, for example, projections which the handling instrument engages from behind.

It is particularly advantageous for the interspace to be arranged in the central area of the side edge, so that the pulling forces can act centrally on the abutment element.

In a preferred embodiment, the interspace is formed by a recess in the abutment element, which is bridged by the pull element.

It is expedient for the abutment element to have a depression above and/or below the pull element for receiving in a guided manner a positioning projection on the handling instrument. It is thereby ensured that in the applied state the handling instrument is placed in a precisely defined position relative to the abutment element, and, therefore, lateral forces can also be applied to the abutment element by the handling instrument, for example, in order to rotate the abutment element about an axis of rotation extending perpendicularly to the abutment surfaces.

It is particularly advantageous for the pull members to be joined to one another at their ends facing away from the pull element, i.e., for the pull element and the pull members to form a structural unit closed within itself.

In particular, it may be provided that the pull members extend around the outer side of the abutment element and thereby lie against its side walls. The abutment element is thus annularly surrounded by the pull element and the pull members, so that the introduced pulling forces subject the material of the abutment element to pressure forces and not to pulling forces. The risk that the abutment element will be damaged by the application of high pulling forces is thereby reduced.

In a modified embodiment, it is also possible for the pull members to extend inside the abutment element at their ends facing away from the pull element. For example, they may be embedded in the material of the abutment element.

In particular, it is advantageous for the pull element and the pull members to be formed by an annular bandage. For example, this may be in the form of a flat band.

Furthermore, it is expedient for a longitudinal groove in which the pull element and the pull members are received to be provided at the side walls of the abutment element. The pull element and the pull members are prevented from displacement by this longitudinal groove. In particular, when pull element and pull members in the form of an annular bandage are used, this extends circumferentially in the longitudinal groove and, where appropriate, may remain in this position after implantation.

Owing to the pulling forces applied to the abutment element upon extracting the abutment element from the implantation site being introduced into it in a distributed manner, and preferably as pressure forces, by virtue of the described construction, the abutment element may consist of a material which has a significantly lower tensile strength than metal, for example, a plastic material which is compatible with the body. In particular, polyetherether-ketone, possibly also carbon fiber reinforced-polyetheretherketone, pyrocarbon or polyethylene with ultrahigh molecular weight are possible.

The intervertebral implant may comprise a single abutment element, which then has an upper outer side and a lower outer side, which are both constructed as surfaces for abutment on adjacent vertebral bodies.

It is, however, also possible for the intervertebral implant to comprise two abutment elements, namely an upper abutment element and a lower abutment element, which are pivotable relative to each other. The upper abutment element then has an upper outer side and the lower abutment element a lower outer side, which are both constructed as surfaces for abutment on adjacent vertebral bodies.

In a one-piece intervertebral implant, it is sufficient to provide the single abutment element with a pull element of high tensile strength. In intervertebral implants with an upper abutment element and a lower abutment element, it is expedient for each abutment element to have a corresponding pull element of high tensile strength.

The invention also relates to a handling instrument for an intervertebral implant of the kind described hereinabove. Such a handling instrument is characterized by having two holding arms arranged in spaced relation to each other, between which the intervertebral implant is arranged in such a way that the holding arms lie against the upper side and the lower side of the abutment element, and by having mounted between the holding arms a slide which is retractable relative to the holding arms and with its end that faces the abutment element engages the pull element from behind in the section containing the interspace.

An abutment element can be grasped between the holding arms with such a handling instrument, and with the slide, which engages the pull element from behind, for example, by means of a hook-shaped projection, a pulling force can then be applied to the pull element, whereby the abutment element can be extracted in its entirety from its position without the risk of damage to the abutment element.

It is expedient for the holding arms to lie clamped against the upper side and the lower side of the abutment element, so that the handling instrument is positioned in a defined manner on the intervertebral implant.

It is also expedient for at least one of the holding arms to enter a depression in the abutment element and to thereby be guided at the sides. Such guidance results in a precisely defined relative positioning of the holding arms and the intervertebral implant.

Furthermore, it is advantageous for a stop to be provided for delimiting the approach of the holding arms in the direction of the displacement of the slide, so that when the slide is retracted, the holding arms can be supported on the intervertebral implant. The slide engaging the pull element from behind is thereby pressed tightly against the pull element and already assumes a defined position in relation to the pull element at the start of the pulling procedure.

The following description of preferred embodiments of the invention serves in conjunction with the drawings for a more detailed explanation.

DETAILED DESCRIPTION OF THE INVENTION

The intervertebral implant 1 shown in FIGS. 1 to 7 comprises an upper abutment element 2 and a lower abutment element 3, which are both of approximately plate-shaped configuration. Both abutment elements 2 and 3 lie with surface-to-surface contact against each other at bearing surfaces. For this purpose, the lower abutment element 3 has a convex, spherical, upwardly projecting bearing surface 4, which enters a complementary, concave bearing surface 5 on the underside of the upper abutment element 2. The two abutment elements 2, 3 are thus pivotable relative to each other, so that their substantially parallel outer sides 6, 7 are adjustable in their inclination to each other. These outer sides 6, 7 form abutment surfaces on adjacent vertebral bodies 8, 9 when the intervertebral implant 1 is pushed into an intervertebral space 10 between the two vertebral bodies 8, 9.

Intervertebral implants 1 of this type of construction are known per se and are often made from metals which are compatible with the body, for example, titanium, titanium alloys or cobalt-chromium-alloys. In the present case, however, both abutment elements 2, 3 are formed from a plastic material that is compatible with the body, for example, polyetheretherketone, a carbon fiber reinforced-polyetheretherketone, a pyrocarbon or an ultrahigh molecular weight polyethylene.

In the embodiment of FIGS. 1 to 5 there extends around the side edges of both the upper abutment element 2 and the lower abutment element 3 in the longitudinal direction a circumferential groove 11 in which there is placed a flat band 12, closed within itself, which is made of metal, for example, of a titanium alloy. At a side edge of the upper abutment element 2, in the illustrated embodiment at the ventral side edge, there is provided an indentation 13 facing inwardly from the ventral side edge, which is bridged by a pull element 28 of the flat band 12, so that an interspace between the pull element 28 and the material of the abutment element 2 is created by the indentation 13 behind the pull element 28 bridging the indentation 13. The flat band 12 disposed within the groove 11 which directly contacts the abutment element comprises pull members engaging opposite sides of the pull element 28.

There is also arranged in the area of this indentation 13 on the outer side 6 of the upper abutment element 2 a depression 14 of substantially rectangular cross section, whose side walls 15 extend parallel to one another in the ventral-dorsal direction.

In a similar manner, the lower abutment element 3 has an indentation 16 and a depression 17 in the outer side 7. This depression 17 also has side walls 18 extending parallel in the ventral-dorsal direction. This indentation 16 is also bridged by the pull element portion 28 of the flat band 12 extending around the lower abutment element 3.

On the inner side, both abutment elements 2, 3 are of flat configuration in the area of the indentations 13, 16 and opposite the depressions 14 and 17. These flat surfaces extend parallel to the respective bottom 19 of the two depressions 14, 17.

Figure 1:
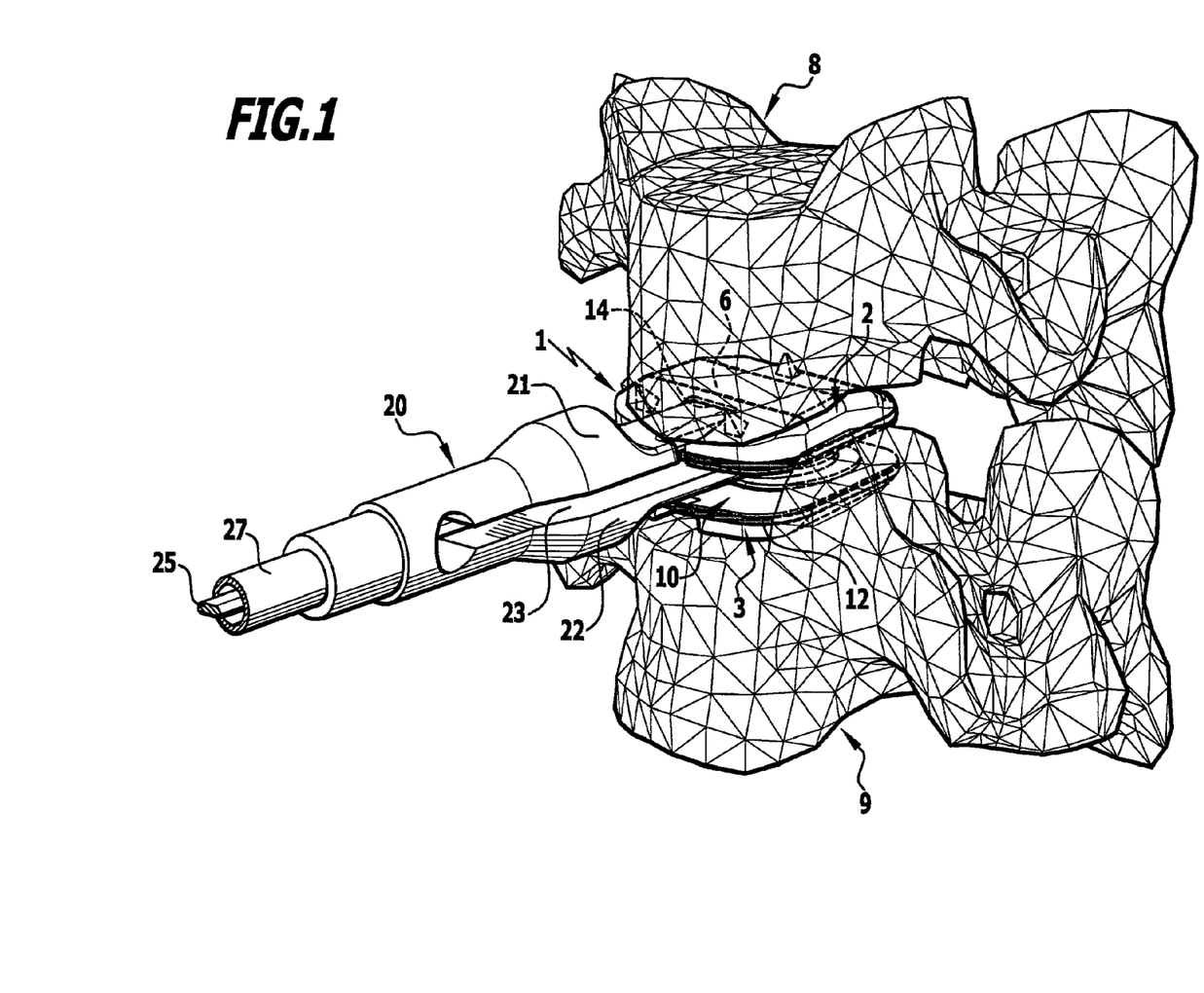
FIG. 1 shows an intervertebral implant connected to a handling instrument in a position in the intervertebral space between two adjacent vertebral bodies.
Figure 2:
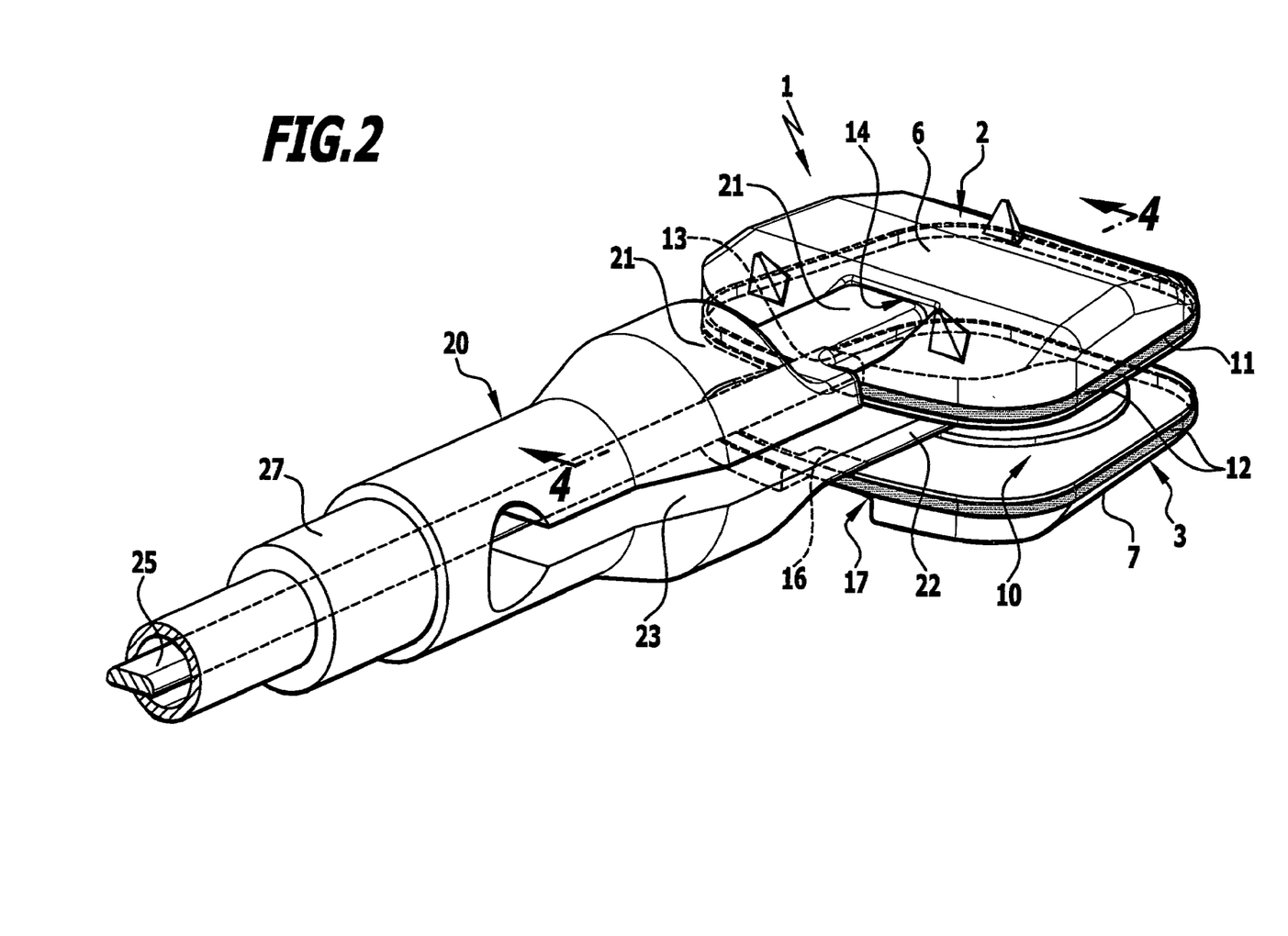
FIG. 2 shows a perspective view of the intervertebral implant of FIG. 1 connected to a handling instrument without the vertebral bodies being represented.
Figure 3:
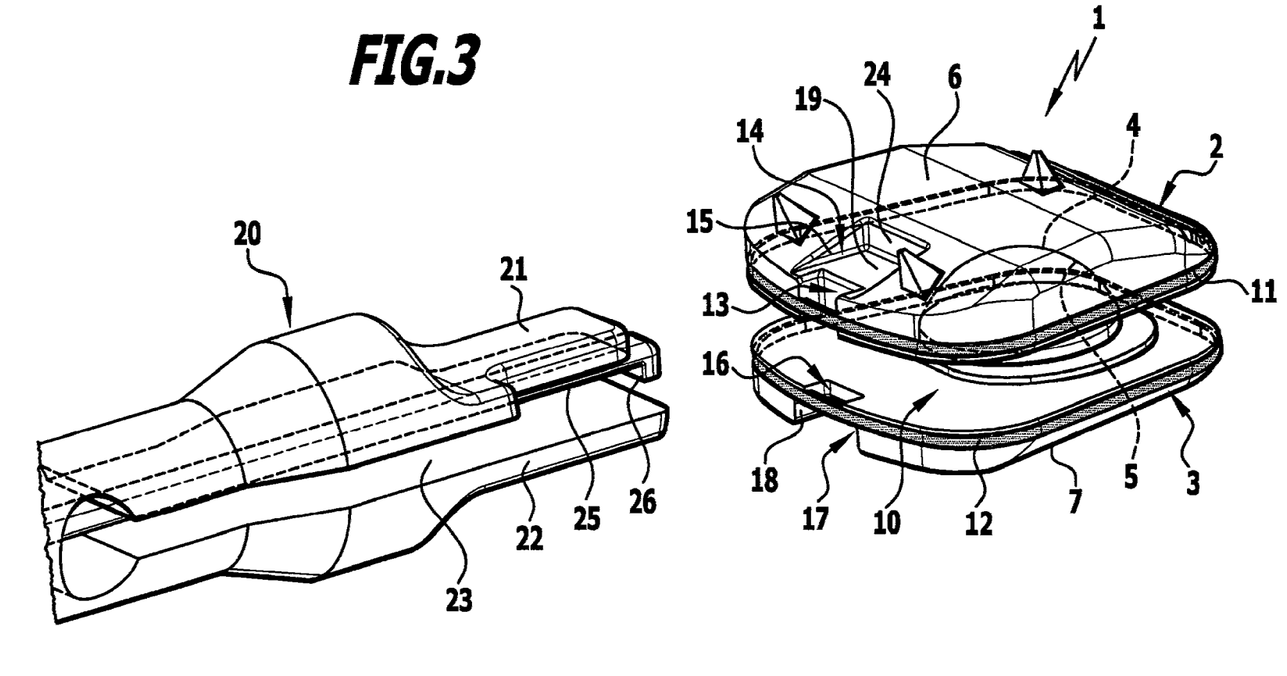
FIG. 3 shows a view similar to FIG. 2 with the handling instrument separated from the intervertebral implant.
Figure 4:
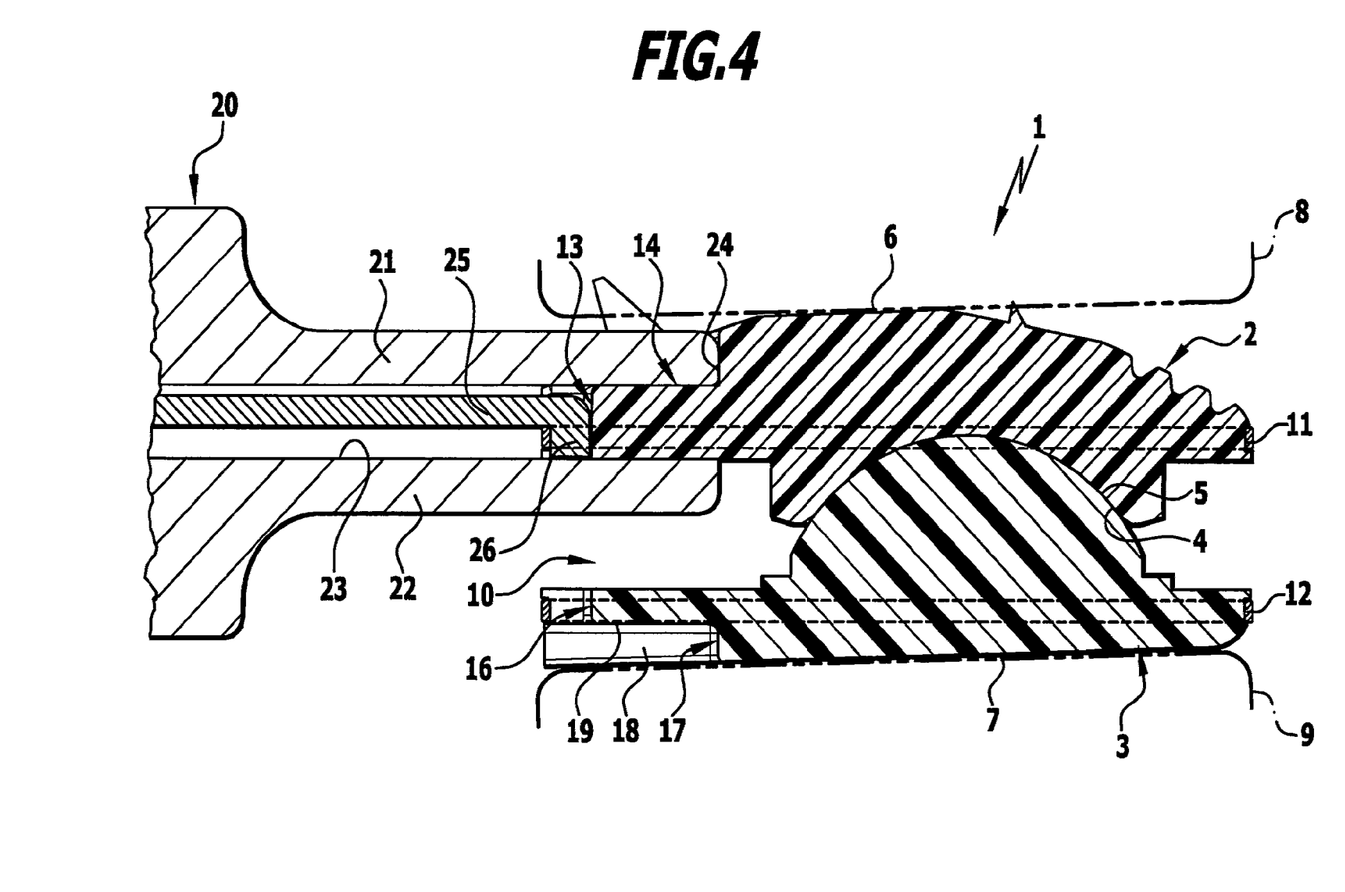
FIG. 4 shows a sectional view taken along line 4-4 in FIG. 2.

An intervertebral implant of this type of construction can be grasped by a handling instrument 20 comprising two arms 21, 22 which are arranged in spaced relation to each other and can be bent apart in a resilient manner. The arms 21, 22 form between them a space 23 into which the abutment element 2 or the abutment element 3 can be pushed in such a way that the two arms 21, 22 engage the bottom 19 of one of the depressions 14 or 17, on the one hand, and the opposite flat inner surface of the abutment elements 2 or 3, on the other hand. The arm of the handling instrument 20 that is located at the outside respectively enters the depression 14 or 17, and the side surfaces of this arm are guided by the side walls 15 or 18 of the recesses 14 and 17. When the arm is completely inserted, it abuts on the rear wall 24 of the depression 14 or the depression 17, so that the insertion depth is thereby delimited. The dimensions are so selected that the two arms 21, 22 are spread apart slightly by the abutment element 2 or 3 pushed into the space 23, and the abutment elements 2, 3 are thereby clampingly secured in the space 23.

Between the two arms 21, 22 of the handling instrument 20 there is mounted for displacement in the longitudinal direction of the arms a slide 25, which carries at its end facing the free end of the arms 21, 22 a projection 26 protruding at one side. This projection 26 can enter the indentation 13 or the indentation 16 behind the pull element 28 and, in this way, engages from behind the pull element 28 bridging the indentation 13 or the indentation 16. Upon further retraction of the slide 25, the pull element 28 and thus the abutment element enclosed by the flat band 12 (pull members) are thereby firmly tensioned against the end face of the arms 21 and 22 of the handling instrument 20. The abutment element is thereby practically fixedly connected to the handling instrument 20. If the handling instrument is now retracted, the pulling force can be transmitted through the slide 25 onto the pull element 28. The pulling forces are then transmitted from the pull element 28 to the flat band extending around the abutment element 2 as pressure forces onto the abutment element and distributed over the circumference of the abutment element 2, so that in spite of use of a plastic material for the abutment element and in spite of the resulting relatively low strength of the material there is no risk of damage occurring to the abutment element even when high pulling forces are applied.

To apply the handling instrument to the intervertebral implant, the slide is first advanced to such an extent that the projection 26 is respectively pushed from the outside into the indentation, and the arms 21, 22, which are mounted on a sleeve 27 of the handling instrument 20 surrounding the slide 25, are then pushed against the abutment element until they reach the rear wall of the respective depression. The projection 26 of the slide 25 is thereby pushed into the indentation and prevented from unintentionally moving out of this indentation. Even in the case of high pulling forces, it is, therefore, ensured that the slide 25 permanently engages the pull element 28 from behind with the projection 26.

Figure 5:
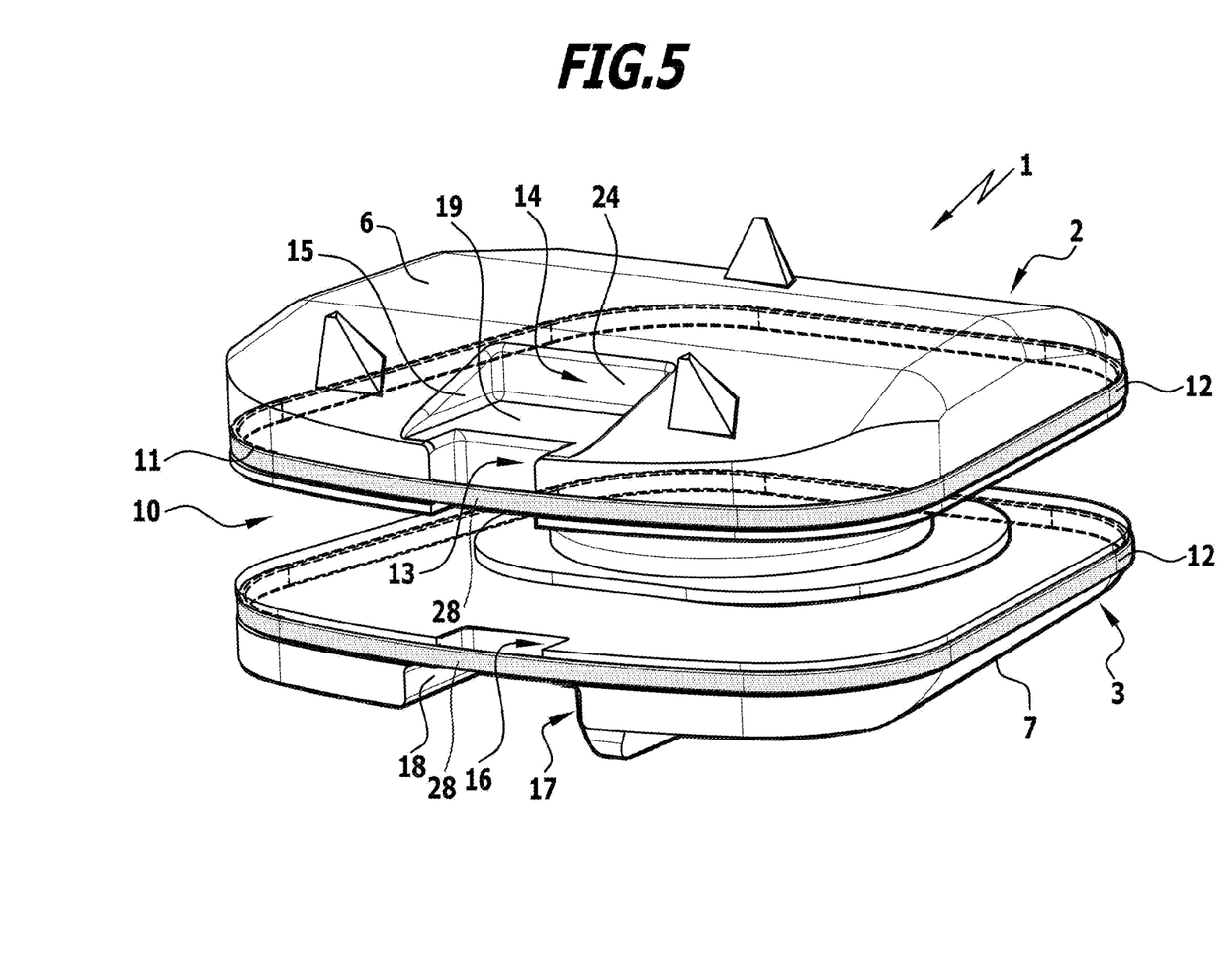
FIG. 5 shows a perspective view of an intervertebral implant with a pull element on both abutment elements in the form of a metallic flat band extending around the outer side of the abutment element.
Figure 6:
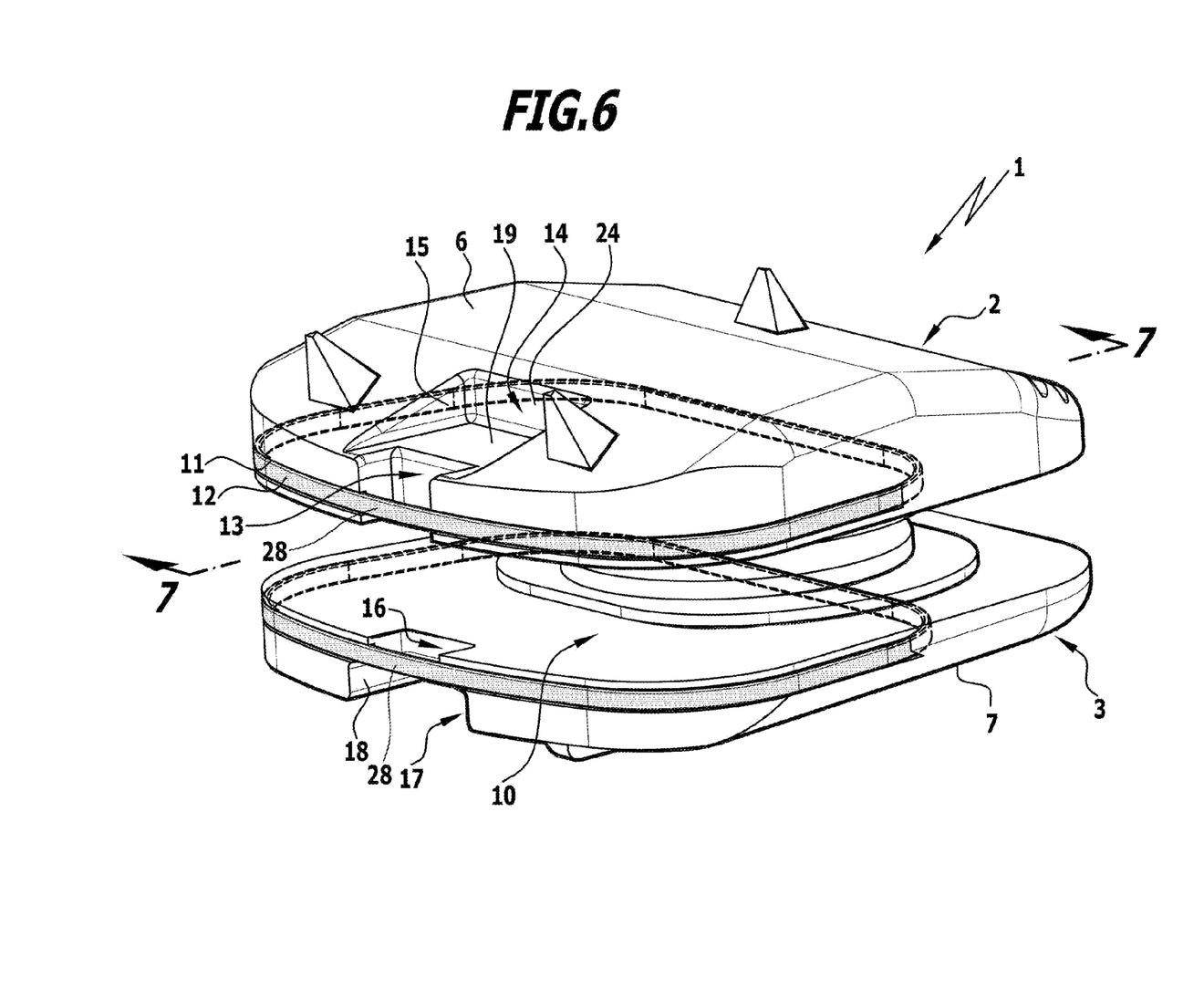
FIG. 6 shows a perspective view similar to FIG. 5 in a modified embodiment of an intervertebral implant with an annular, band-shaped pull element extending partially through the abutment element.
Figure 7:
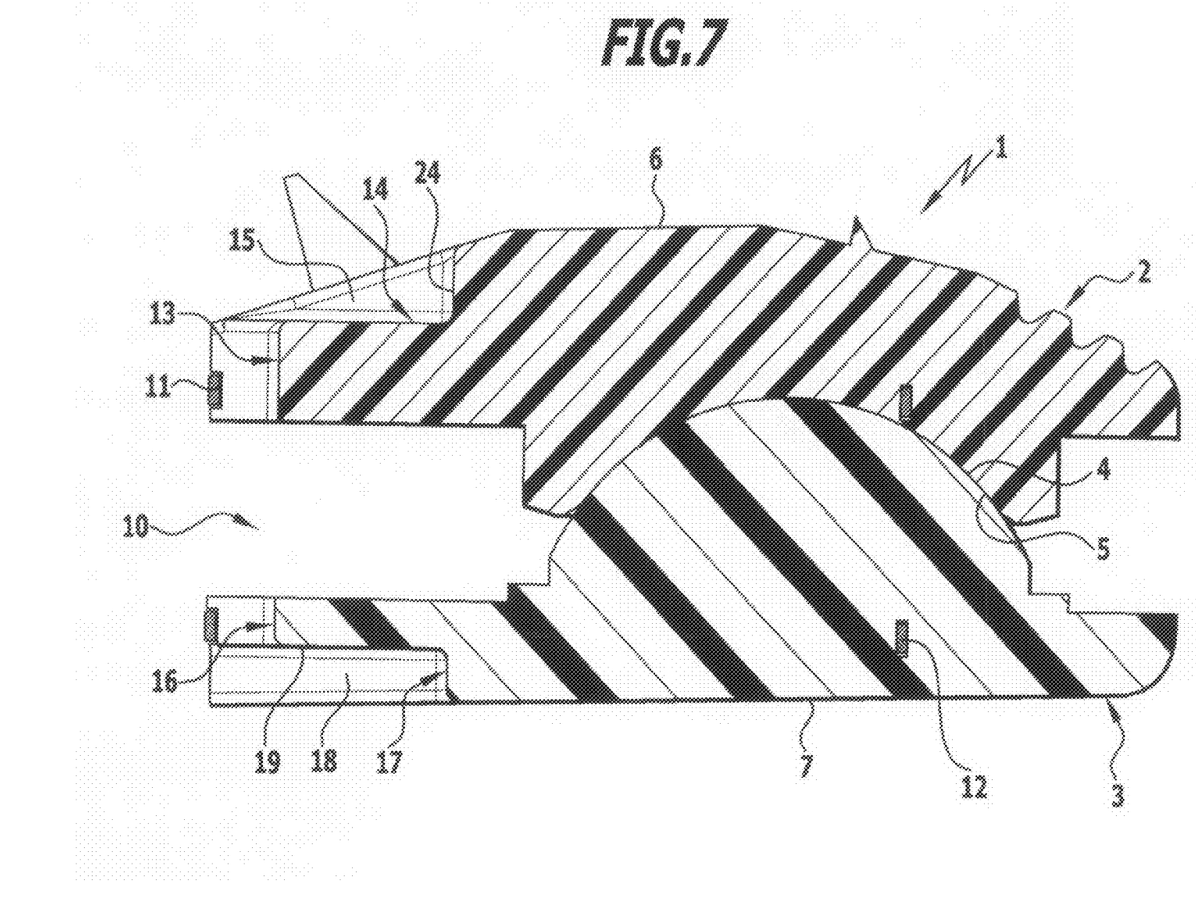
FIG. 7 shows a sectional view taken along line 7-7 in FIG. 6.

The embodiment of FIGS. 6 and 7 of the intervertebral implant is essentially of the same construction as the embodiment of FIG. 5. Corresponding parts are, therefore, given the same reference numerals. Differently from the embodiment of FIG. 5, the flat band 12 in this embodiment does not extend over its entire length on the outer side of the abutment element, but only in the area of the ventral side edge and in the ventral section of the two adjoining side edges extending transversely thereto. In the dorsal section, however, the flat band 12 extends through the abutment element, i.e., it is embedded in the plastic material of the abutment element. As is evident from this, the bandage consisting of the flat band 12 does not necessarily need to completely surround the abutment element, it also being possible for only substantial portions of the abutment element to be engaged by it. A complete encircling is nevertheless advantageous when particularly high pulling forces have to be applied as the abutment element does then not have to be subjected to pulling forces in sections thereof.

In the embodiments of FIGS. 1 to 7, the intervertebral implant comprises two abutment elements, namely an upper abutment element 2 and a lower abutment element 3.

Figure 8:
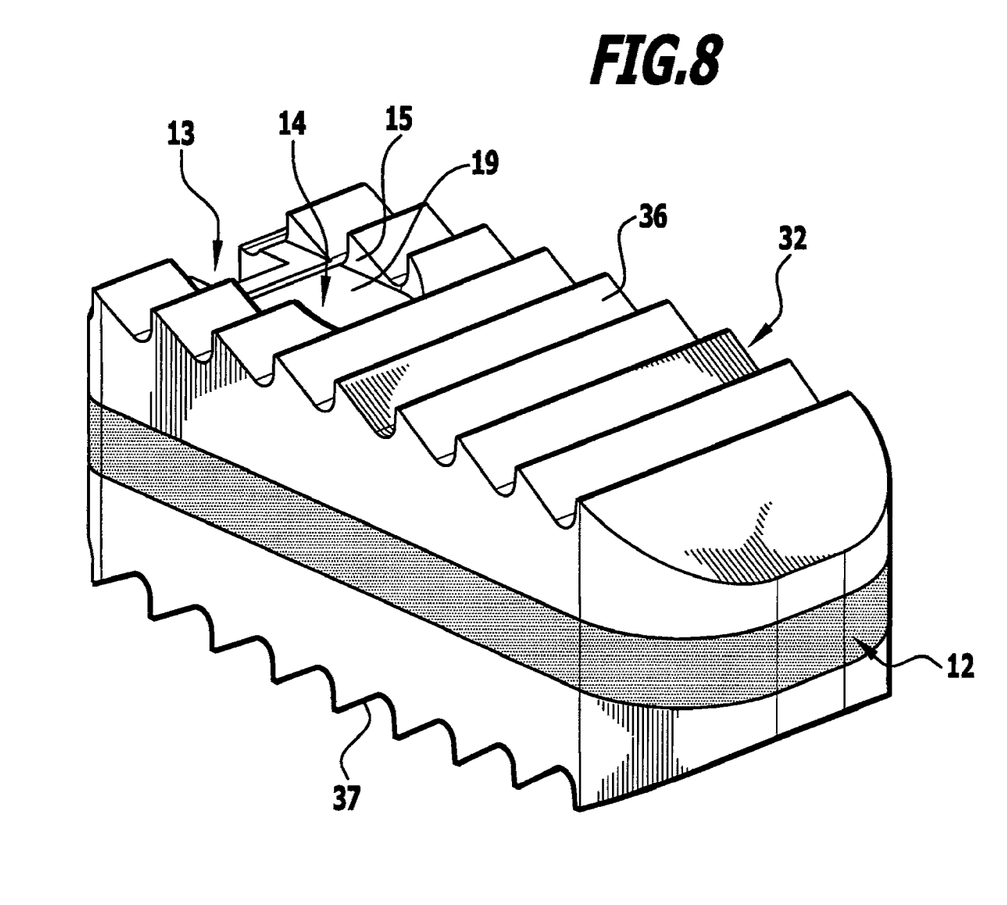
FIG. 8 shows a perspective view of an intervertebral implant with a single abutment element and a pull element extending around it.
Figure 9:
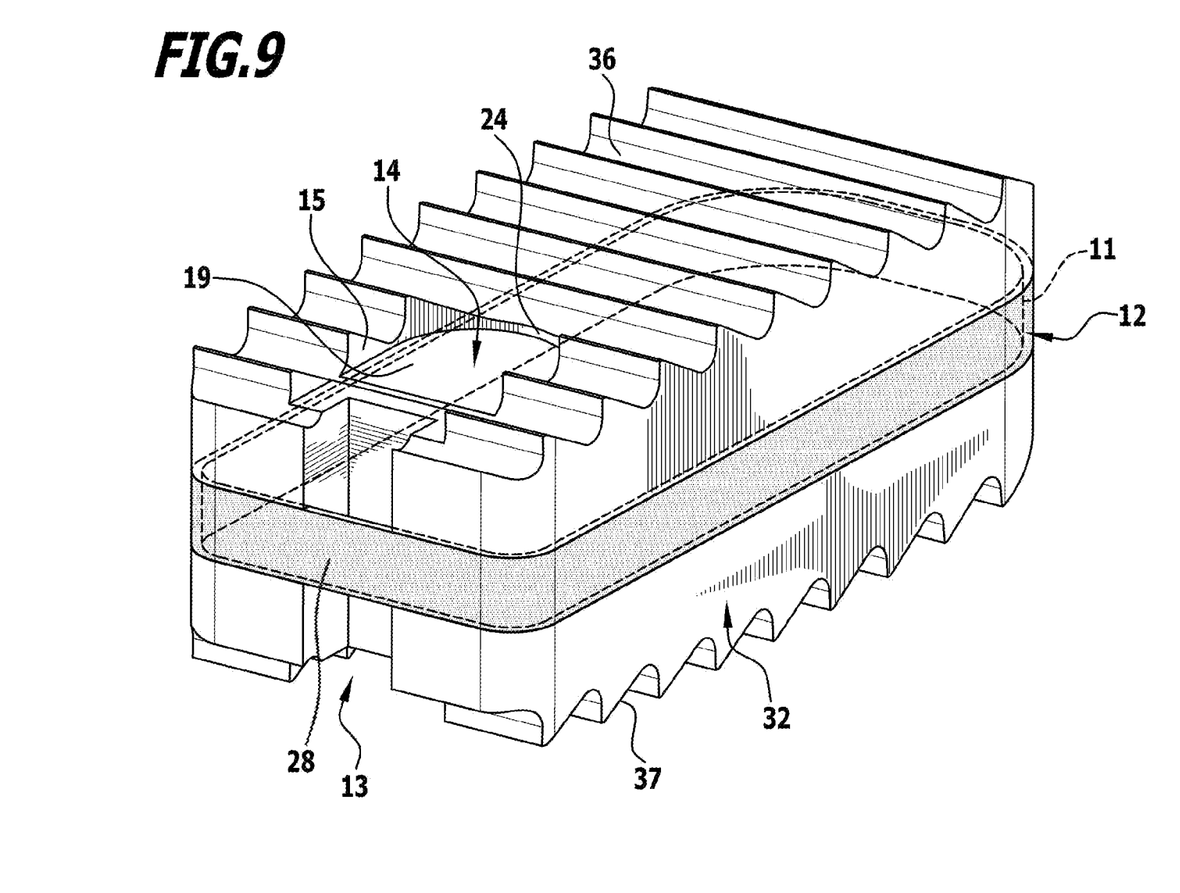
FIG. 9 shows a perspective view of the intervertebral implant of FIG. 8 seen from the opposite side.

In contrast to this, there is provided in the intervertebral implant of FIGS. 8 and 9 only a single abutment element 32, whose upper outer side 36 forms an upper abutment surface and whose lower outer side 37 forms a lower abutment surface, which can both be placed against adjacent vertebral bodies. In this implant, the abutment element is therefore a supporting body which is pushed into the intervertebral space and extends over the entire height of the intervertebral space.

In other respects, a construction similar to that of the two abutment elements 2, 3 of FIGS. 1 to 7 is chosen. Corresponding parts are therefore given the same reference numerals.

The invention claimed is:

1. Intervertebral implant, comprising:
   an abutment element for abutment on at least one vertebral body,
   a pull element extending along a side edge of the abutment element,
   pull members holding the pull element on the abutment element, said pull members extending along sides of the abutment element in a direction towards an opposite side edge, said pull element being made of a material whose tensile strength is greater than a tensile strength of a material of the abutment element, and
   an interspace for receiving a handling instrument for engaging the pull element from behind, the interspace being arranged at least in a section along the pull element between said pull element and said abutment element;
   wherein the interspace is formed by a recess in the abutment element, which recess is bridged by the pull element.

2. Intervertebral implant in accordance with claim 1, wherein the interspace is arranged in a central area of the side edge.

3. Intervertebral implant in accordance with claim 1, wherein the abutment element has a depression at least one of above and below the pull element for receiving in a guided manner a positioning projection on the handling instrument.

4. Intervertebral implant in accordance with claim 3, wherein the pull members extend around an outer side of the abutment element and thereby lie against its side edges.

5. Intervertebral implant in accordance with claim 1, wherein the pull members are joined to one another at ends facing away from the pull element.

6. Intervertebral implant in accordance with claim 5, wherein the pull element and the pull members are formed by an annular bandage.

7. Intervertebral implant in accordance with claim 6, wherein the bandage is in a form of a flat band.

8. Intervertebral implant in accordance with claim 1, wherein the pull members extend inside the abutment element at ends facing away from the pull element.

9. Intervertebral implant in accordance with claim 1, wherein a longitudinal groove for receiving the pull element and the pull members is provided at the side edges of the abutment element.

10. Intervertebral implant in accordance with claim 1, wherein the pull element consists of metal.

11. Intervertebral implant in accordance with claim 1, wherein the abutment element consists of a plastic material.

12. Intervertebral implant in accordance with claim 1, wherein the abutment element has an upper outer side and a lower outer side, which are both constructed as surfaces for abutment on adjacent vertebral bodies.

13. Intervertebral implant in accordance with claim 1, wherein the abutment element comprises an upper abutment element and a lower abutment element, which are pivotable relative to each other, said upper abutment element having an upper outer side, and said lower abutment element having a lower outer side, which are both constructed as surfaces for abutment on adjacent vertebral bodies.

* * * * *